United States Patent
Goodwin et al.

(10) Patent No.: US 11,480,540 B2
(45) Date of Patent: Oct. 25, 2022

(54) RUTHENIUM ALLOYS FOR BIOSENSORS

(71) Applicant: Materion Corporation, Mayfield Heights, OH (US)

(72) Inventors: Kevin V. Goodwin, Torrington, CT (US); Robert R. Newton, West Simsbury, CT (US); Ian S. Tribick, Groton, MA (US); Ethan Fontaine, Hartford, CT (US)

(73) Assignee: MATERION CORPORATION, Mayfield Heights, OH (US)

( * ) Notice: Subject to any disclaimer, the term of this patent is extended or adjusted under 35 U.S.C. 154(b) by 131 days.

(21) Appl. No.: 16/867,705

(22) Filed: May 6, 2020

(65) Prior Publication Data

US 2020/0309724 A1    Oct. 1, 2020

Related U.S. Application Data

(63) Continuation of application No. 15/817,547, filed on Nov. 20, 2017, now Pat. No. 10,775,334.

(60) Provisional application No. 62/424,911, filed on Nov. 21, 2016, provisional application No. 62/451,948, filed on Jan. 30, 2017.

(51) Int. Cl.
| | |
|---|---|
| *G01N 27/327* | (2006.01) |
| *C22C 5/04* | (2006.01) |
| *C12Q 1/00* | (2006.01) |
| *C23C 14/35* | (2006.01) |
| *C23C 14/20* | (2006.01) |
| *C22C 27/00* | (2006.01) |
| *G01N 27/30* | (2006.01) |

(52) U.S. Cl.
CPC ........ *G01N 27/3271* (2013.01); *C12Q 1/001* (2013.01); *C22C 5/04* (2013.01); *C22C 27/00* (2013.01); *C23C 14/20* (2013.01); *C23C 14/205* (2013.01); *C23C 14/352* (2013.01); *G01N 27/301* (2013.01); *G01N 27/327* (2013.01)

(58) Field of Classification Search
CPC .............. G01N 27/327–3272; G01N 27/3275
See application file for complete search history.

(56) References Cited

U.S. PATENT DOCUMENTS

| | | |
|---|---|---|
| 6,180,416 B1 | 1/2001 | Kurnik |
| 6,284,013 B1 | 9/2001 | Shindo et al. |
| 6,554,920 B1 | 4/2003 | Jackson et al. |

(Continued)

FOREIGN PATENT DOCUMENTS

| | | |
|---|---|---|
| CN | 100405051 | 7/2008 |
| CN | 103913489 A | 7/2014 |

(Continued)

OTHER PUBLICATIONS

Santos et al., "Rat Cerebrospinal Fluid Treatment method through Cisterna Cerebellomedullaris Injection," Neurosci. Bull. Oct. 2018, 34(5):827-832 (Year: 2018).*

(Continued)

*Primary Examiner* — Alexander S Noguerola
(74) *Attorney, Agent, or Firm* — Tucker Ellis LLP

(57) ABSTRACT

The present disclosure relates to metal alloys for biosensors. An electrode is made from ruthenium metal or a ruthenium-based alloy. The resulting electrode has physical and electrical property advantages when compared with existing pure metal electrodes.

20 Claims, 14 Drawing Sheets

(56) References Cited

U.S. PATENT DOCUMENTS

| | | | |
|---|---|---|---|
| 7,455,756 | B2 | 11/2008 | Choi et al. |
| 2003/0148141 | A1 | 8/2003 | Zhao et al. |
| 2003/0198859 | A1* | 10/2003 | Ritts .................. C07K 14/00 |
| | | | 429/401 |
| 2004/0038072 | A1 | 2/2004 | Miura |
| 2009/0283805 | A1 | 11/2009 | Chou et al. |
| 2010/0163432 | A1* | 7/2010 | Marinesco ............ C12Q 1/005 |
| | | | 204/403.14 |
| 2012/0118735 | A1 | 5/2012 | Kim et al. |
| 2013/0306494 | A1 | 11/2013 | Miyazaki |
| 2013/0345534 | A1 | 12/2013 | Hoss |
| 2014/0061044 | A1* | 3/2014 | Thekkedath ....... A61B 5/14532 |
| | | | 204/403.01 |
| 2015/0129422 | A1* | 5/2015 | Harada ............... H01J 37/3426 |
| | | | 204/298.13 |
| 2015/0247816 | A1 | 9/2015 | Bhansali |

FOREIGN PATENT DOCUMENTS

| | | |
|---|---|---|
| JP | 2016173376 | 9/2016 |
| TW | I223064 | 11/2004 |
| TW | 200819745 | 5/2008 |
| TW | 201007164 | 2/2010 |
| WO | WO 2017/112688 A1 | 6/2017 |

OTHER PUBLICATIONS

Kumari et al., perivascular CSF flow in the rat cerebellum, Journal of Clinical Neuroscience (1999) 6(2), 143-146 (Year: 1999).*

Murtas et al., "Biochemical Properties of Human D-Amino Acid Oxidase," Frontiers in Molecular Biosciences Dec. 2017| vol. 4| Article 88 (Year: 2017).*

Daly et al., The use of polymers coupled with metallised electrodes to allow H2O2 detection in the presence of electrochemical interferences, Taianta 49 (1999) 667-678 (Year: 1999).*

Li et al., "Electrocatalytic Oxidation of Glucose at Carbon Nanotubes Supported PtRu Nanoparticles and Its Detection," Electroanalysis 20, 2008, No. 20, 2212-2216 (Year: 2008).*

Shim et al., "Nonenzymatic Amperometric Glucose Sensor Based on Nanoporous Gold/Ruthenium Electrode," Electroanalysis 2011, 23, No. 9, 2057-2062 (Year: 2011).*

Yang et al., "A novel non-enzymatic glucose sensor on Pt3Ru1 alloy nanoparticles with high density of surface defects," Biosensors and Bioelectronics 80 (2016) 171-174 (Year: 2016).*

Search Report for Taiwan Applicaiton No. 106140282 and translation; dated May 7, 2021; 12 pages.

Daly et al., The use of polymers coupled with metallised electrodes to allow H2O2 detection in the presence of electrochemical interferences, Talanta 49 (1999) 667-678 (Year: 1999).

Kelly et al., "Development of an interferant free amperometric biosensor for determination of L-lysine in food," Analytica Chemical Acta 412 (2000) 111-119 (Year: 2000).

Ashley G., Patentability of alloys at the European Patent Office, Intellectual Prop., May 31, 1997, pp. 3-6, vol. 2, No. 3, XP007922941.

International Search Report dated May 24, 2018 for Application Serial No. PCT/US2017/062495 (6 pages).

International Written Opinion dated May 24, 2018 for Application Serial No. PCT/US2017/062495 (8 pages).

* cited by examiner

RUTHENIUM ALLOYS FOR BIOSENSORS

CROSS-REFERENCE TO RELATED APPLICATIONS

This application is a continuation of U.S. patent application Ser. No. 15/817,547, filed Nov. 20, 2017, now U.S. Pat. No. 10,775,334, which claims priority to U.S. Provisional Patent Application Ser. No. 62/424,911, filed Nov. 21, 2016, and to U.S. Provisional Patent Application Ser. No. 62/451,948, filed Jan. 30, 2017. The entirety of these applications are incorporated fully by reference.

BACKGROUND

The present disclosure relates to metal alloys; electrodes, for example, physical vapor deposited components for electrodes such as those found in biosensors; and methods for creating a biosensor. In particular, the biosensors have one or more electrodes made from a non-noble metal alloy, such as a ruthenium based alloy in combination with elements such as aluminum (Al), chromium (Cr), copper (Cu), molybdenum (Mo), nickel (Ni), rhenium (Re), and tungsten (W), having desired mechanical and electrical properties, and will be described with particular reference thereto. However, it is to be appreciated that the present disclosure is also amenable to other like applications.

Biosensors can be used in several applications, such as for measuring the amount of an analyte (e.g., glucose) in a biological fluid (e.g., blood). Blood glucose monitoring is a valuable tool in the management of diabetes. Diabetes is a disease in which the body is unable to control tightly the level of blood glucose, which is the most important and primary fuel of the body. This is due to either the pancreas not producing enough insulin, or to the cells of the body not responding properly to the insulin produced. Patients with diabetes are encouraged to monitor their glucose levels to prevent hyperglycemia, as well as other long-term complications such as heart disease, stroke, kidney failure, foot ulcers, and eye damage. A glucose biosensor is an analytical device for detecting the analyte, glucose, in the blood. Although glucose biosensors have been devised based on potentiometry, amperometry, and colorimetry, to date most commercially available biosensors are amperometric biosensors. These biosensors use a redox enzyme (e.g., glutathione peroxidases (GPX), nitric oxide synthase (eNOS, iNOS, and nNOS), peroxiredoxins, super oxide dismutases (SOD), thioredoxins (Trx), and the like), as the biological component responsible for the selective recognition of the analyte of interest (e.g., glucose).

A biosensor of this type is a relatively small strip of laminated plastic that can be exposed to a biological sample such as blood. An important feature of the biosensor is that it is disposable and only used one time. The strip acts as a substrate for a reaction chamber and two electrodes, a reference electrode and a working electrode, which are connected to the reaction chamber. The glucose biosensor contains a reagent layer that is attached to the working electrode. The reagent layer includes the selective recognition component (i.e., the redox enzyme) as well as electron mediators.

An electron mediator is an artificial electron transferring agent that helps shuttle electrons from the redox enzyme to the electrode surface. The mediator does this by reacting with the reduced enzyme and then diffusing to the electrode surface. Examples of mediators include vinyl ferrocene (VFc) initiated by 2,2'-azobisisobutyronitrile (AIBN), osmium complexes, quinone, ferricyanide, methylene blue, 2,6-dichloroindophenol, thionine, gallocyanine, indophenol, combinations thereof, and the like.

The biological fluid sample is introduced into the reaction chamber of the glucose biosensor and the biosensor is connected to a measuring device such as a meter for analysis using the biosensor's electrodes. The analyte (glucose) in the sample undergoes a reduction/oxidation reaction at the working electrode (where the redox enzyme is located) while the measuring device applies a biasing potential signal through the electrodes of the biosensor. The redox reaction produces an output signal in response to the biasing potential signal. The output signal usually is an electronic signal, such as potential or current, which is measured and correlated with the concentration of the analyte in the biological fluid sample.

Electrodes in such biosensors are typically made from expensive precious metals, such as silver, gold, palladium, or platinum. It would be desirable to develop new alloys that can be used as electrodes in a biosensor that have additional advantages when used with specific enzyme/mediator systems. It would also be desirable if such alloys did not include precious metals, which are costly.

BRIEF DESCRIPTION

The present disclosure relates to biosensors having electrodes formed from a metal alloy, such as a ruthenium-based alloy. A reagent is disposed on the electrode, the reagent comprising specific combinations of an enzyme and an electron mediator. The resulting electrode has physical and/or electrical properties that are advantageous when used with the reagent. These properties can include thinness, safety during reaction with the redox reagent, electrical conductivity, and reactivity with the redox reagent. While most of this disclosure relates to electrodes used as biosensor components, it is contemplated that the electrodes can be used in other end-use applications as well. As a result, any disclosure herein related to electrodes used in biosensors is intended to incorporate herein applicability to all electrodes that this technology could reasonably be applied to by one of ordinary skill in the art.

Disclosed in various embodiments are metal alloys comprising ruthenium in combination with at least one additional alloying element. It is contemplated that the ruthenium-containing alloy may be a binary, ternary, or quaternary alloy.

In some particular embodiments, the alloy may contain from about 5 atomic percent (at %) to about 95 at % ruthenium, including 50 at % or greater ruthenium; about 5 at % to about 45 at % ruthenium; from about 50 at % to about 95 at % ruthenium; about 55 at % to about 95 at % ruthenium; about 50 at % to about 65 at % ruthenium; from about 50 at % to about 60 at %; about 55 at % to about 75 at % ruthenium; from about 60 at % to about 70 at %; about 65 at % to about 85 at % ruthenium; from about 70 at % to about 80 at %; about 75 at % to about 95 at % ruthenium; from about 80 at % to about 90 at %; or about 85 at % to about 95 at % ruthenium. This is on the basis of the alloy totaling 100 at %.

In other particular embodiments, the alloy contains from about 95 atomic percent (at %) to less than 100 at % ruthenium, including about 95 at % to about 96 at % ruthenium; from about 96 at % to about 97 at % ruthenium; about 97 at % to about 98 at % ruthenium; and about 98 at % to about 99 at % ruthenium. The additional alloying element(s) are present in a total amount of greater than zero at % to about 5 at %. This is on the basis of the alloy totaling 100 at %.

The additional alloying element(s) are, in particular embodiments, selected from the group consisting of aluminum, chromium, copper, nickel, rhenium, and tungsten.

In particular embodiments, the alloy may contain ruthenium in combination with about 5 at % to about 95 at % of the additional alloying element(s), including about 55 at % to about 95 at %; about 5 at % to about 50 at %; about 35 at % to about 50 at %; from about 40 at % to about 50 at %; about 25 at % to about 45 at %; from about 30 at % to about 40 at %; about 15 at % to about 35 at %; from about 20 at % to about 30 at %; about 5 at % to about 25 at %; from about 10 at % to about 20 at %; or about 5 at % to about 15 at %; or from about 0 at % to about 10 at % of the additional alloying element(s). In particular embodiments when the ruthenium-based alloy is a ternary alloy, the weight ratio of the first alloying element to the second alloying element may be from about 1:1: to about 2:1.

In other particular embodiments, the alloy may contain ruthenium in combination with greater than zero to about 5 at % of the additional alloying element(s), including about 1 at % to about 2 at %; about 2 at % to about 3 at %; about 3 at % to about 4 at %; and from about 4 at % to about 5 at %. In particular embodiments when the ruthenium-based alloy is a ternary alloy, the weight ratio of the first alloying element to the second alloying element may be from about 1:1: to about 2:1.

In some particular embodiments, the alloy is a binary alloy of (a) ruthenium and (b) either chromium or tungsten. These binary alloys may comprise about 55 at % to about 85 at % ruthenium, remainder chromium or tungsten; or about 55 at % to about 65 at % ruthenium, remainder chromium or tungsten; or about 75 at % to about 85 at % ruthenium, remainder chromium or tungsten.

In some particular embodiments, the alloy is a binary alloy of (a) ruthenium and (b) aluminum. These binary alloys may comprise about 60 at % to about 70 at % ruthenium, remainder aluminum; or about 15 at % to about 25 at % ruthenium, remainder aluminum.

In some particular embodiments, the alloy is a binary alloy of (a) ruthenium and (b) nickel. These binary alloys may comprise about 5 at % to about 25 at % ruthenium, remainder nickel.

In some particular embodiments, the alloy is a ternary alloy of (a) ruthenium and (b) nickel and aluminum. These binary alloys may comprise about 20 at % to about 55 at % ruthenium, remainder nickel and aluminum combined.

In some particular embodiments, the alloy is a ternary alloy of (a) ruthenium and (b) chromium and tungsten. These binary alloys may comprise about 20 at % to about 55 at % ruthenium, remainder chromium and tungsten combined.

Also disclosed herein are biosensors, electrodes, and articles comprising such alloys or ruthenium metal.

Also disclosed in various embodiments are methods of creating a biosensor, comprising: forming a first electrode from a ruthenium-based alloy on a surface of a substrate. The ruthenium-based alloys can include any of the aforementioned alloys.

The methods can further comprise forming the first electrode by co-sputtering.

The methods can additionally comprise forming a reaction chamber in the substrate, the reaction chamber contacting the first electrode. In addition, a reagent layer can be formed on the first electrode to form a working electrode.

The methods contemplate that the first electrode operates as a reference electrode, and further comprise forming a second electrode on the substrate from the binary ruthenium-based alloy, and placing a reagent layer on the second electrode to form a working electrode.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
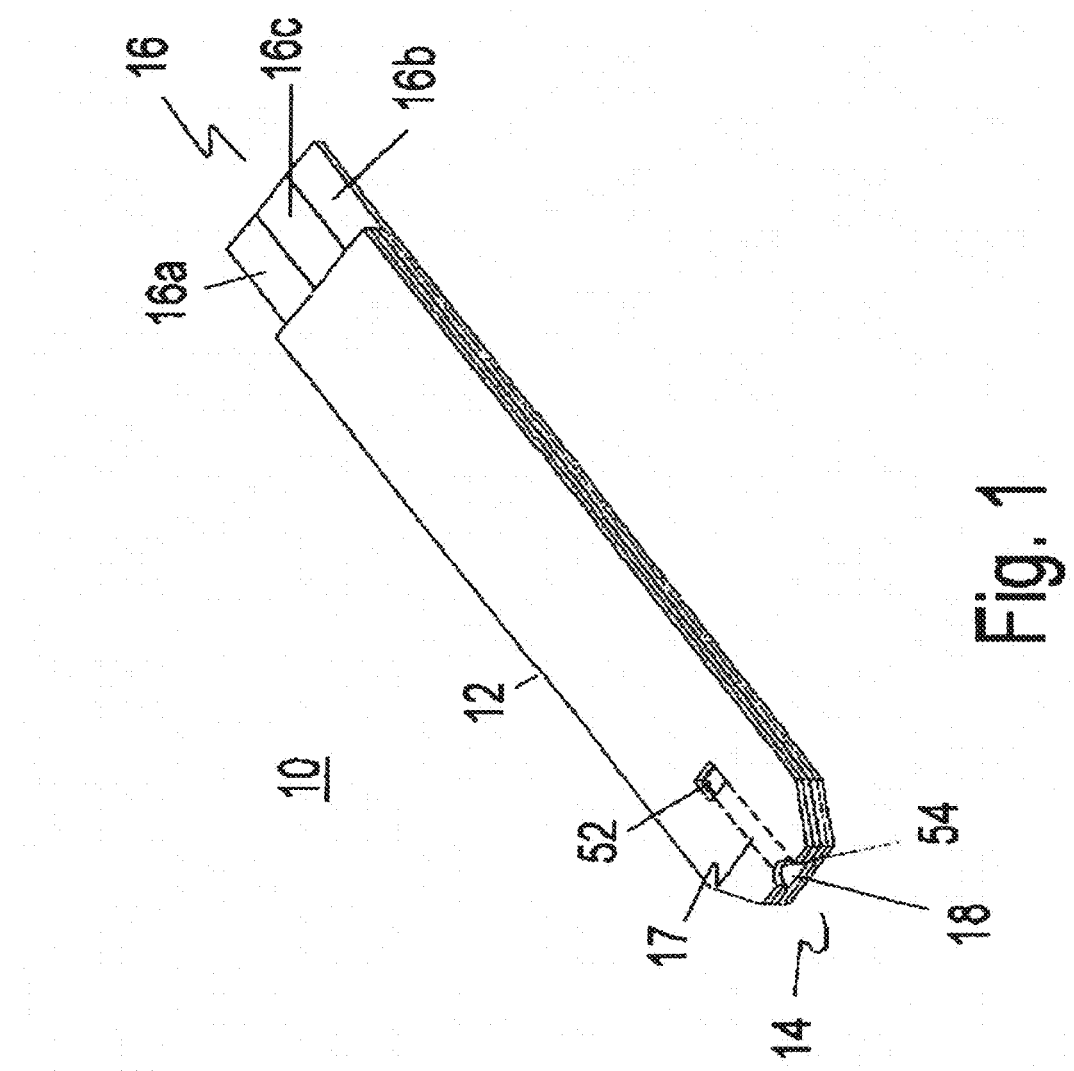
FIG. 1 is a perspective view of an exemplary biosensor of the present disclosure.

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

References to "one embodiment," "an embodiment," or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, step, etc. described in one embodiment may also be included in other embodiments, but is not necessarily included. Thus, the present technology can include a variety of combinations and/or integrations of the embodiments described herein.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

A value modified by a term or terms, such as "about" and "substantially," may not be limited to the precise value specified. The modifier "about" should also be considered as disclosing the range defined by the absolute values of the two endpoints. For example, the expression "from about 2 to about 4" also discloses the range "from 2 to 4."

It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

The term "reagent" and variants thereof refers to a composition that may include multiple ingredients. For example, the reagent is sometimes used herein to described a composition containing a redox enzyme, electron mediators, and additional substances/compounds. A reagent can be liquid or solid.

The present disclosure is generally directed to a component for an electrode such as those used in a biosensor. As used herein, the term "biosensor" shall denote a device for analyzing biological samples. In some embodiments, the biosensor may be a medical sensor, such as a glucometer, and the biosensor component may comprise a test-strip for use with the biosensor. As used herein, the term "medical sensor" shall denote a biosensor used for medical monitoring and/or diagnosis.

The phrase "ruthenium metal" is used herein to refer to a metal that is made only of ruthenium, and may contain incidental impurities, i.e. contains 100 at % ruthenium.

A biosensor is typically formed from: (1) a substrate; (2) a pair of electrodes; and (3) a reagent layer that reacts with the analyte, and generally contains the redox enzyme and electron mediators.

In the present disclosure, at least one electrode is formed from either a metal alloy, ruthenium metal, or a metal alloy containing a quantity of ruthenium. The metal alloy generally does not include precious metals such as gold, silver, palladium, or platinum. This makes the biosensor cheaper, which increases market opportunities for the biosensor. These alloys can be used to provide physical and electrical property advantages when used with specific enzyme/mediator systems. Such physical and electrical properties may include thinness of the electrode, better electrical conductivity, stability over time, physical contact durability, lowered contact resistance for lowered/more consistent bias response, and/or better cohesion for finer line formation in circuitry. In particular embodiments, the metal alloy is a ruthenium-based alloy.

FIG. 1 is a perspective view of a biosensor 10. The biosensor 10 has a body 12, a fluid sampling end 14, an electrical contact end 16, and a vent opening 52. A notch 54 is disposed at the fluid sampling end 14 to facilitate loading of the fluid sample into the sample chamber 17. The fluid sampling end 14 includes a sample chamber 17 between a sample inlet 18 and the vent opening 52. The electrical contact end 16 has three discrete conductive contacts 16a, 16b, and 16c.

Figure 2:
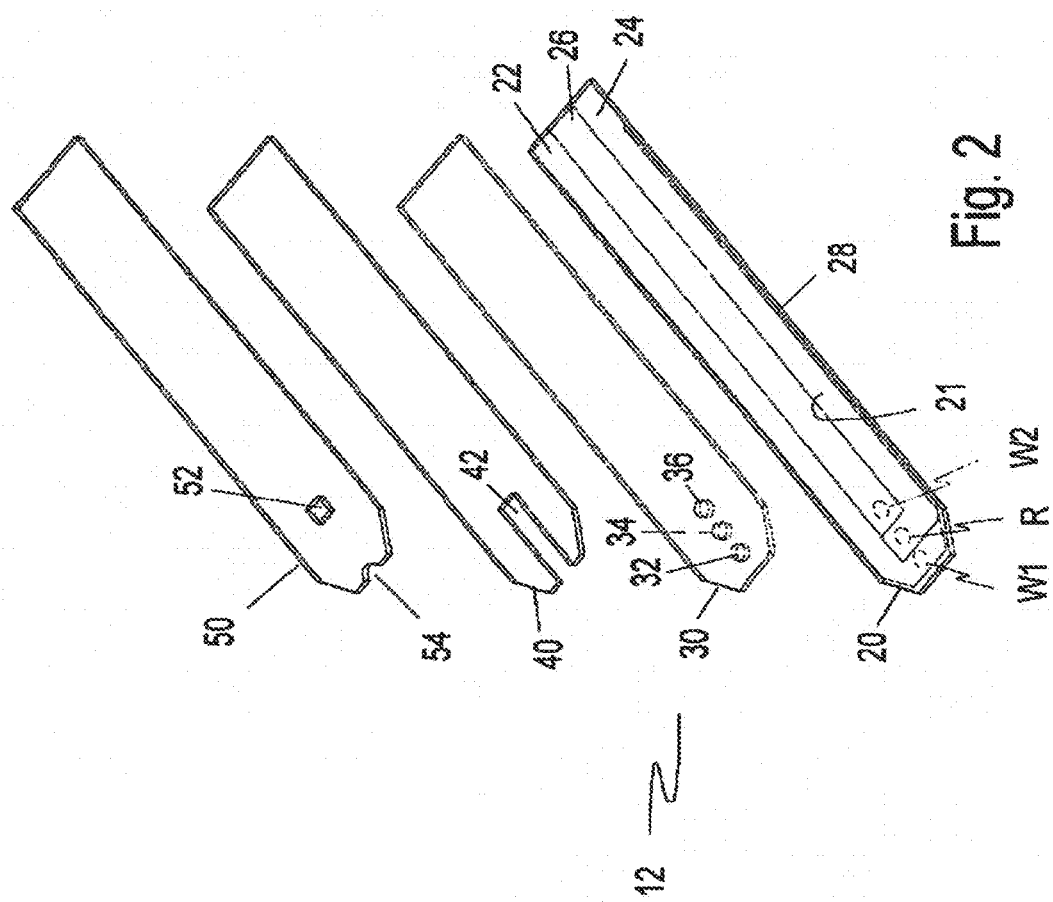
FIG. 2 is an exploded view of the biosensor of FIG. 1.

FIG. 2 is an exploded view of the biosensor 10. The body 12 is composed of a substrate 20, an optional reagent holding layer 30, a channel forming layer 40, and a cover 50. The layers of the body 12 are generally made of plastics such as polyvinyl chloride, polycarbonate, polysulfone, nylon, polyurethane, cellulose nitrate, cellulose propionate, cellulose acetate, cellulose acetate butyrate, polyester, polyimide, polypropylene, polyethylene and polystyrene. Other polymer compositions known in the art include: nylon, polyesters, copolyesters, polyethylene, polypropylene, polyamides; polystyrene, polystyrene copolymers, styrene acrylonitrile copolymers, acrylonitrile butadiene styrene copolymers, poly(methylmethacrylate), acrylic copolymers, poly(ether-imides); polyphenylene oxides or poly(phenylene oxide)/polystyrene blends, polystyrene resins; polyphenylene sulfides; polyphenylene sulfide/sulfones; poly (ester-carbonates); polycarbonates; polysulfones; polysulfone ethers; and poly(ether-ketones); or mixtures of any of the other foregoing polymers. These materials may be either flexible or rigid, and should be generally non-conductive and chemically inert to the contemplated chemical reactions described herein.

The substrate 20 has a metal film 21 on which are delineated three electrodes 22, 24 and 26. The electrodes 22, 24, 26 may be formed by scribing or scoring the metal film 21, or by silk-screening electrodes 22, 24, 26 onto the substrate 20. Scribing or scoring of the metal film 21 may be done by mechanically scribing the metal film 21 sufficiently to create the three independent electrodes 22, 24, 26. The preferred scribing or scoring method of the present disclosure is done by using a carbon dioxide laser, a YAG laser or an excimer laser. Alternatively, the metal film is patterned as it is laid down, such that the metal film forms one electrode.

Yet another method for forming an electrode for a biosensor comprises (a) providing a substrate; (b) providing a target; and (c) physical vapor depositing at least a portion of said substrate with material from said target to thereby form a conductive layer (i.e. electrode) on said substrate. Physical vapor deposition techniques include sputter coating (e.g., magnetron sputtering, unbalanced magnetron sputtering, facing targets sputtering, or the like), thermal evaporation, electron beam evaporation, laser ablation, arc vaporization, co-evaporation, ion plating, or the like. As illustrated here, three different films would be deposited to form the three electrodes 22, 24, 26.

The reagent holding layer 30 can be used when liquid reagents are desired to be used. The reagent holding layer 30 has three reagent holding openings 32, 34 and 36. The reagent holding opening 32 exposes a portion of the electrode 22, the reagent holding opening 34 exposes a portion of the electrode 24, and the reagent holding opening 36 exposes a portion of the electrode 26 creating reagent holding wells. This layer 30 is used to hold a sufficient quantity of chemical reagents in liquid form and to promote capillary action through the sample chamber of the sensor. The reagent holding layer 30 may be made from a plastic sheet and may be coated with a pressure sensitive adhesive, a photopolymer, ultrasonically-bonded to substrate 20, or silk-screened onto the substrate 20.

Usually, the channel forming layer 40 has a U-shaped cutout 42 located at the fluid sampling end 14. The length of the cutout 42 is such that when the channel forming layer 40 is laminated to reagent holding layer 30, electrode areas W and R are within the space defined by the cutout 42. The length, width and thickness of the U-shaped cutout 42 define the capillary channel volume.

The three reagent holding openings 32, 34, 36 define electrode areas W1, W2, and R, respectively, and hold chemical reagents forming two working electrodes and one reference electrode. Generally, the electrode areas are loaded with the reagent mixtures. The reagent mixtures for the working electrode areas 32, 34, 36 are a mixture of enzymes and redox mediators with optional polymers, surfactants, and buffers. A reference reagent matrix may be loaded in electrode area R that is similar to the reagent mixture of the working electrodes. It is contemplated that W1 and W2 use different enzymes/mediators, which can be used to check each other. Embodiments are also contemplated that have only one working electrode, which may be simpler to manufacture.

Alternatively, the chemical reagents can be used to form a reagent layer in the form of a dried solid film on the electrode areas W1, W2, R. In these embodiments, the reagent holding layer 30 is not needed.

Typically, electrode area R must be loaded with a redox reagent or mediator to make the reference electrode function. The reference reagent mixture preferably contains either oxidized or a mixture of an oxidized and reduced form of redox mediators, at least one binder, a surfactant and an antioxidant (if a reduced form of redox mediator is used) and a bulking agent. In the alternative, the reference electrode (electrode area R) could be also loaded with a Ag/AgCl layer (e.g. by applying Ag/AgCl ink or by sputter-coating a Ag or Ag/AgCl layer) or other reference electrode materials that do not require a redox mediator to function properly.

The size of the reagent holding openings is desirably as small as possible while still being capable of holding sufficient chemical reagent to function properly. As depicted here, the reagent holding openings are round and have a preferred diameter of about 0.03 in. (0.76 mm). The three reagent holding openings 32, 34, 36 are aligned with each other and are spaced about 0.025 in. (0.625 mm) from each other. The circular reagent holding openings are for illustrative purposes only and it should be understood that the shape of the reagent holding openings is not critical.

When a fluid sample is applied to a single strip of the present disclosure, the fluid sample enters the channel through the sampling end aperture and flows over W1, W2 and R and stops at the threshold of the vent opening. Chronoamperometry (i-t curve) can be used to measure the current response of the biosensor. Oxygen concentration ($pO_2$) can be controlled. Once a blood sample enters the strip, a potential of 0.3-0.5 volts is applied across the working electrodes and the reference electrode. The glucose concentration of the blood sample can then be measured.

The above described embodiments are based on amperometric analyses. Those skilled in the art, however, will recognize that a sensor of the present disclosure may also utilize coulometric, potentiometric, voltammetric, and other electrochemical techniques to determine the concentration of an analyte in a sample.

Figure 3:
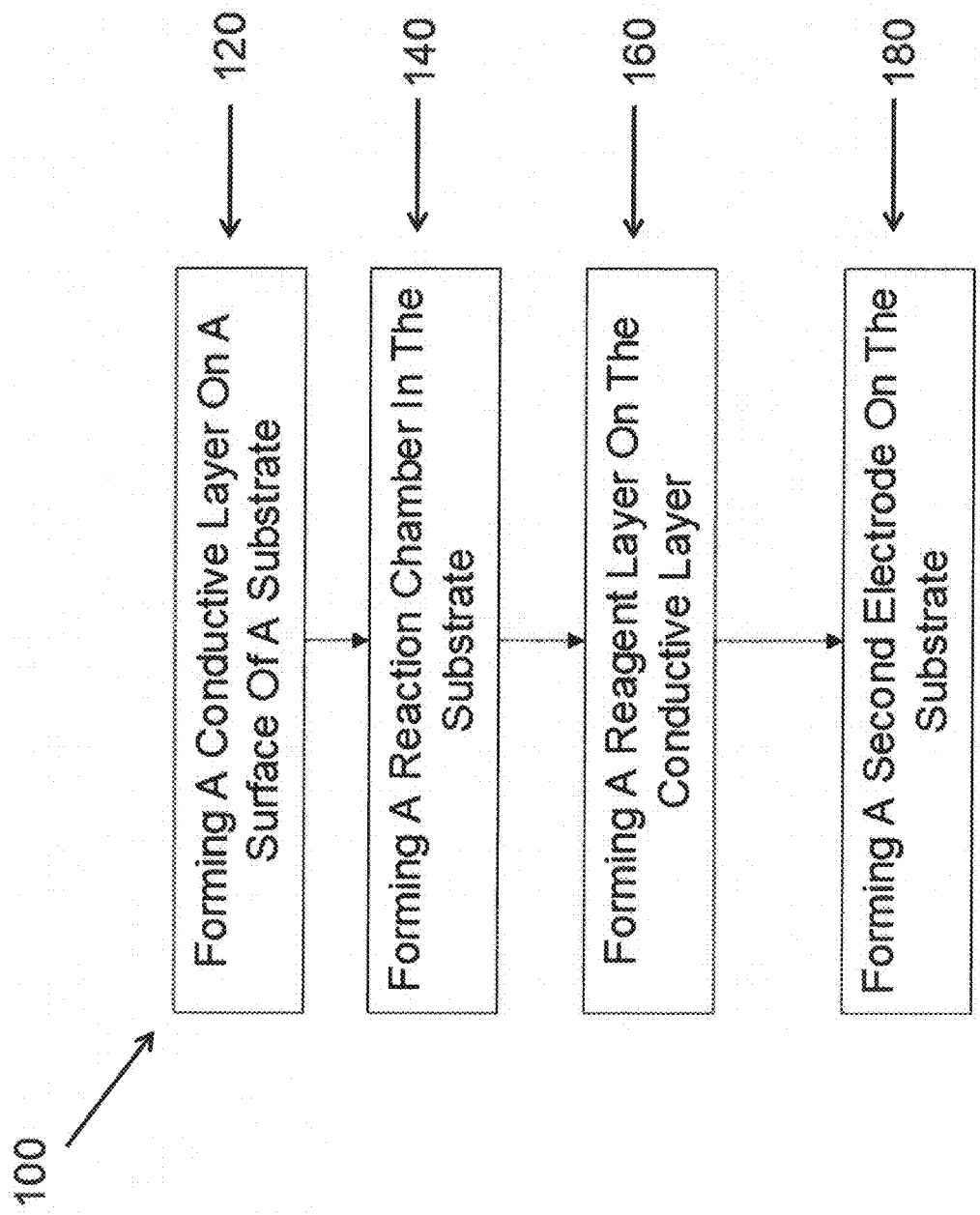
FIG. 3 is a flow chart illustrating an exemplary method of the present disclosure.

FIG. 3 is a flowchart that illustrates an exemplary method 100 of creating a biosensor with an electrode made from a metal alloy. The method 100 includes the steps of: forming a conductive layer on a surface of a substrate in which the conductive layer includes a metal alloy (Step 120); forming a reaction chamber in the substrate in which the reaction chamber contacts the conductive layer (Step 140); forming a reagent layer on the conductive layer to form a working electrode (Step 160); and forming a second electrode on the substrate (Step 180).

At Step 120, a conductive layer is formed on a surface of a substrate in which the conductive layer includes the metal alloy. In some instances, the conductive layer is sputtered onto a surface of a substrate. For example, the conductive layer is deposited onto the substrate surface by using fast ions to eject particles of the metal from a conductive material source due to contact of the metal source by energetic particles. The conductive layer can be used to form a single electrode, or can be shaped or patterned to form two or more electrodes. In specific embodiments, the metal alloy is a ruthenium-based alloy.

At Step 140, a reaction chamber is formed in the substrate in which the reaction chamber contacts the conductive layer. The reaction chamber can be formed in the substrate by any method known in the art.

At Step 160, a reagent layer is formed on the conductive layer to form a working electrode. The reagent layer can be formed on the conductive layer by any method known in the art. More particularly, the reagent layer contains an enzyme, a coenzyme, and an electron mediator. Specific enzyme/mediator systems are contemplated. In a first system, the enzyme is glucose oxidase (GOD), the coenzyme is flavin adenine dinucleotide (FAD), and the mediator is hexacyanoferrate (II)/hexacyanoferrate. In a second system, the enzyme is glucose dehydrogenase (GDH), the coenzyme is pyrroloquinoline quinone (PQQ), and the mediator is hexacyanoferrate (II)/hexacyanoferrate. In a third system, the enzyme is GDH, the coenzyme is PQQ, and the mediator is quinoneamine/phenylenediamine.

At Step 180, a second electrode is formed on the substrate. The second electrode can be formed as described in Step 120.

The metal alloy itself can be a binary, ternary, or quaternary alloy of suitable metals. In particular embodiments, the alloy is a metal alloy containing ruthenium (Ru) in combination with one or more additional alloying element(s). The alloy may contain from about 5 atomic percent (at %) to about 95 at % ruthenium, including 50 at % or greater ruthenium; about 5 at % to about 45 at % ruthenium; from about 50 at % to about 95 at % ruthenium; about 55 at % to about 95 at % ruthenium; about 50 at % to about 65 at % ruthenium; from about 50 at % to about 60 at %; about 55 at % to about 75 at % ruthenium; from about 60 at % to about 70 at %; about 65 at % to about 85 at % ruthenium; from about 70 at % to about 80 at %; about 75 at % to about 95 at % ruthenium; from about 80 at % to about 90 at %; or about 85 at % to about 95 at % ruthenium.

It is particularly contemplated that the alloys used herein are metal alloys containing ruthenium (Ru) in combination with one or more elements such as aluminum (Al), chromium (Cr), copper (Cu), nickel (Ni), rhenium (Re), or tungsten (W). The alloy may contain from about 5 at % to about 95 at % of these additional alloying element(s), including about 55 at % to about 95 at %; about 5 at % to about 50 at %; about 35 at % to about 50 at %; from about 40 at % to about 50 at %; about 25 at % to about 45 at %; from about 30 at % to about 40 at %; about 15 at % to about 35 at %; from about 20 at % to about 30 at %; about 5 at % to about 25 at %; from about 10 at % to about 20 at %; or about 5 at % to about 15 at %; or from about 0 at % to about 10 at % of the additional alloying element(s).

As mentioned above, it is also contemplated that the electrode of the biosensor can be made from ruthenium metal (i.e. 100 at % ruthenium), or a metal alloy that contains a high content of ruthenium, such as from about 95 at % to less than 100 at % ruthenium.

The high content ruthenium metal alloy itself can be a binary, ternary, or quaternary alloy of suitable metals. In particular embodiments, the alloy is a metal alloy containing ruthenium (Ru) in combination with one or more additional alloying element(s). The alloy may contain from about 95 atomic percent (at %) to less than 100 at % ruthenium, including about 95 at % to about 96 at % ruthenium; from about 96 at % to about 97 at % ruthenium; about 97 at % to about 98 at % ruthenium; or about 98 at % to about 99 at % ruthenium.

It is particularly contemplated that the alloys used herein are metal alloys containing a high content of ruthenium (Ru) in combination with one or more elements such as aluminum (Al), chromium (Cr), copper (Cu), nickel (Ni), rhenium (Re), or tungsten (W). The alloy may contain from greater than zero at % to about 5 at % of these additional alloying element(s), including about 1 at % to about 2 at %; about 2 at % to about 3 at %; about 3 at % to about 4 at %; and from about 4 at % to about 5 at % of the additional alloying element(s).

Any combination of ruthenium with one or more of the other elements at the compositional ranges specified above is contemplated. The alloy may be formed using a cluster (i.e., co-sputtering) system with the substrate rotation disabled to allow a range of compositions over the wafer area. Desirably, one would fabricate a sputtering target from the alloy, as this allows deposition uniformity to be maintained.

In particular embodiments, the alloy is a binary metal alloy containing ruthenium in combination with either chromium or tungsten. In further particular embodiments, the metal alloy is a binary alloy combining ruthenium (Ru) with aluminum (Al). In additional embodiments, the metal alloy is a binary alloy combining ruthenium (Ru) with nickel (Ni). In other additional embodiments, the metal alloy includes ruthenium (Ru) with rhenium (Re).

In some particular embodiments, the alloy is a binary metal alloy containing ruthenium in combination with either chromium or tungsten. These binary alloys may comprise about 55 at % to about 85 at % ruthenium, or about 55 at % to about 65 at % ruthenium, or about 75 at % to about 85 at %. The remainder of these binary alloys is chromium or tungsten.

In further particular embodiments, the metal alloy is a binary alloy combining ruthenium (Ru) with aluminum (Al). The alloy may contain from about 5 at % to about 45 at % ruthenium, or from about 55 at % to about 95 at % ruthenium, with the remainder being aluminum. In particular embodiments, the alloy may contain about 60 at % to about 70 at % ruthenium and about 30 at % to about 40 at % aluminum.

In additional embodiments, the metal alloy is a binary alloy combining ruthenium (Ru) with nickel (Ni). The alloy may contain from about 55 at % to about 95 at % ruthenium and from about 5 at % to about 45 at % nickel.

In other additional embodiments, the metal alloy includes ruthenium (Ru) with rhenium (Re). The alloy may contain from about 55 at % to about 95 at % ruthenium and from about 5 at % to about 45 at % rhenium.

As one skilled in the art would readily appreciate, the metal alloys may comprise incidental impurities. As used herein, "incidental impurities" refer to any impurities that naturally occur in the ore used to produce the metal alloys or that are inadvertently added during the production process.

The resulting electrode(s) formed from the metal alloy desirably exhibit improved physical and electrical properties. One improved property is the thickness of the electrode, which can be very thin. In embodiments, the electrode can have a thickness of about 10 nanometers to about 100 nanometers. Another improved property is the electrical conductivity of the electrode, which can be less than 100 ohms/square ($\Omega$/sq) at the desired thickness. The biosensor may also exhibit improved stability, as measured by electrochemical response stability over time when exposed to humidity and temperature variations, or as measured by changes in adhesion and/or abrasion differences when exposed to the reagent. Other desirable properties can include physical contact durability, lowered contact resistance for lowered/more consistent bias response, and/or better cohesion for finer line formation in circuitry. In addition, the resulting electrode(s) formed from the ruthenium-based alloy can be produced at a lower cost compared to more expensive metals such as gold.

As previously mentioned, the electrode can be formed by physical vapor deposition. This generally describes the coating of the substrate with the material from the non-noble metal alloy target to form the conductive layer. As used herein, the term "physical vapor deposition" shall denote depositing thin-films by providing for the condensation of vaporized material onto a substrate. The physical vapor deposited coating may be performed with any type of physical vapor deposition process previously described, i.e., sputter coating, thermal evaporation, electron beam evaporation, laser ablation, arc vaporization, co-evaporation, ion plating, or the like. For example, in some embodiments, the physical vapor depositing step will be performed via a sputtering process, in which the substrate is coated with the conductive layer by sputtering the non-noble metal alloy target via the sputtering device. The resulting substrate with the conductive layer coated thereon may be used as a biosensor component, which may include a working electrode, a reference electrode, or a counter electrode. In certain embodiments, such as when a roll of substrate material is vacuum coated with a conductive layer, via a roll-to-roll physical vapor deposition process, the resulting thin-film sheet may be cut apart to appropriate size to form a thin-film electrode upon a substrate. In other embodiments, the biosensor components can be formed from the thin-film sheet by etching, such as chemical or laser etching. In still other embodiments, the biosensor components can be formed using a patterned mask, which is laid on the substrate, and the conductive layer is physical vapor deposited thereover to form the biosensor component.

In certain specific embodiments, the biosensor components may be created via a roll-to-roll physical vapor deposition process that includes roll-to-roll magnetron sputtering. For instance, a substrate sheet comprising a polymer film made of PET (polyethyleneptrapthalate) with a thickness ranging from 25 μm to 250 μm and width of 33.02 cm may be sputtered using a 77.50 cm wide web roll-to-roll magnetron sputter coater. A single or a dual target configuration can be employed to deposit a conductive layer of metal alloys. A target comprised of a non-noble metal alloy plate can be used. A vacuum chamber of the sputter coater can be pumped down to base pressure of at least $10^{-5}$ Torr using a diffusion and mechanical pump combination. In other embodiments a combination of a mechanical pump, a turbo pump, a cryo pump, and/or an oil diffusion pump may be used. Magnetron sputtering cathodes housing the non-noble metal alloy targets having a generally rectangular shape of 15.24 cm×30.48 cm can be energized using 2 KW power supplies (such as offered from Advanced Energy Inc.). An argon gas flow into the vacuum chamber can be controlled (such as via a MKS model 1179A flow controller) to set a sputtering pressure between 3 to 10 mTorr for use during the sputtering process.

A thickness and sheet resistance of the sputtered conductive layer can be efficiently controlled in-situ by controlling the roll-to-roll web speeds, i.e., controlling the speed of the substrate sheet as it travels through the vacuum chamber during sputtering. For example, for sputtering of a conductive layer of Composition A3,the web speed can be set to between 0.1 to 3.5 meters per minute and sputtering power density of between 2 to 8 Watts per square cm. As such, sputtered conductive layer of Composition A3 may be formed having a measured thickness value of about 25 nm and a sheet resistance of about 45 ohms per square.

EXAMPLES

Example 1

The performance of existing biosensors utilizing electrodes made from precious metals, such as gold (Au) and palladium (Pd), was compared with the performance of electrodes made from ruthenium or ruthenium-based alloys disclosed herein. At the sputter stage, test samples of PET were cut to a 4-inch wafer shape. A conductive layer including ruthenium was sputtered using a DC magnetron "cluster" (co-sputtering) sputter system, with the substrate rotation disabled to allow a range of compositions over the wafer area. Target thickness was between about 300 and about 400 angstroms (Å). The process pressure was about 3 mTorr argon (Ar), with an argon gas flow of about 55 standard cubic centimeters per minute (sccm). The target to substrate distance was about 67 mm.

Cyclic Voltammetry (CV) analysis was selected to detect changes in performance, with a baseline performance based on pure gold electrodes. The CV test method measured faradaic current generated by the reduction of oxidation of substances near the electrode, including cathodic peak current (Ipc), anodic peak current (Ipa), cathodic peak potential (Epc), and anodic peak potential (Epa). For combinatorial alloy deposition, an additional Si wafer was used to facilitate energy-dispersive X-ray spectroscopy (EDS) compositional analysis, or X-ray powder diffraction (XRD) characterization as required. Samples were handled and packaged using best practices to avoid contamination from contact with the sputtered area.

The test electrode samples were serialized within wafers to identify sample position, as well as serialized for wafer lot identification number. The initial test included at least 10 samples per wafer with locations distributed across the wafer. The Cyclic Voltammetry (CV) test parameters are summarized in Table 1 below:

TABLE 1

Initial CV test parameter (screening) summary

| Test Parameter | Description | Value | Notes |
| --- | --- | --- | --- |
| $H_2SO_4$ conc. | Sulfuric acid cleaning solution concentration | 0.1M | Used with potential scan to initially clean electrode of contamination. |
| KCl conc. | Potassium Chloride electrolyte concentration | 0.1M | — |
| $K_4Fe(CN)_6$ conc. | Potassium ferrocyanide analyte concentration | 1 mM | — |
| Sample volume | Volume of tested solution | 20 μL | — |
| Waveform/ Scan range | Potential range | −0.5 V to 0.3 V | — |
| Scan rate | Rate of potential change | 50 mV/s | |
| Test repeats | # of repeated scans (same electrode) | 6 or greater | Can abort scans after 3 if no redox response detected |

Electrodes were singulated in strips using a paper cutter, then manually singulated from the strips with scissors. The electrodes were placed in a test fixture and connected to a BASi potentiostat and analyzer. Cyclic voltammetry (CV) was performed using 1 nM of $K_4Fe(CN)_6$ concentration in 0.1 M KCl. Peak current (IP), Ipc, Ipa, Epc, and Epa were recorded as well as a qualitative assessment.

First, the ferro/ferri electrochemical response of pure metal thin-film depositions was evaluated in the range of test parameters listed in Table 1 above and established for screening. The assessment of pure depositions is shown below in Table 2:

TABLE 2

Assessment of pure metal thin-film depositions

| Bulk Density (g/cc) | Sputter rate (nm/s) | Sputter yield | *= Redox | Background current (est.) (uA) | Qualitative Notes |
|---|---|---|---|---|---|
| 20.53 | 12 | 0.9 | Re | 1 | Variable - smooth |
| 19.35 | 8 | 0.6 | W | 3 | Smooth response |
| 19.31 | 32 | 2.8 | Au* | — | Good redox |
| 16.6 | 8.5 | 0.6 | Ta | 0.1 | Flat |
| 12.3 | 18 | 1.3 | Ru* | — | Good redox, background current |
| 12.02 | 27 | 2.4 | Pd* | — | Good redox, changes over multiple scans |
| 10.2 | 12 | 0.9 | Mo | 10 | Smooth response, large starting current |
| 8.92 | 32 | 2.3 | Cu | 1 | Noisy, variable. Reaction at 100 mV |
| 8.9 | 19 | 1.5 | Ni* | — | Good redox, secondary reaction |
| 8.9 | 19 | 1.4 | Co | 1 | Variable - flat |
| 8.57 | 8 | 0.6 | Nb | 1 | Smooth response |
| 7.86 | 18 | 1.3 | Fe | 10 | Smooth response |
| 7.3 | 80 | — | In | — | |
| 7.2 | 32 | 1.3 | Cr | 1 | Oxidation peak |
| 6.49 | 8.5 | 0.7 | Zr | 0 | Flat |
| 5.75 | 80 | — | Sn | — | |
| 4.5 | 8 | 0.6 | Ti | 0.1 | Flat |
| 2.7 | 17 | 1.2 | Al | 1 | Variable - flat, noisy |
| 2.37 | — | — | B | — | |

Figure 4:
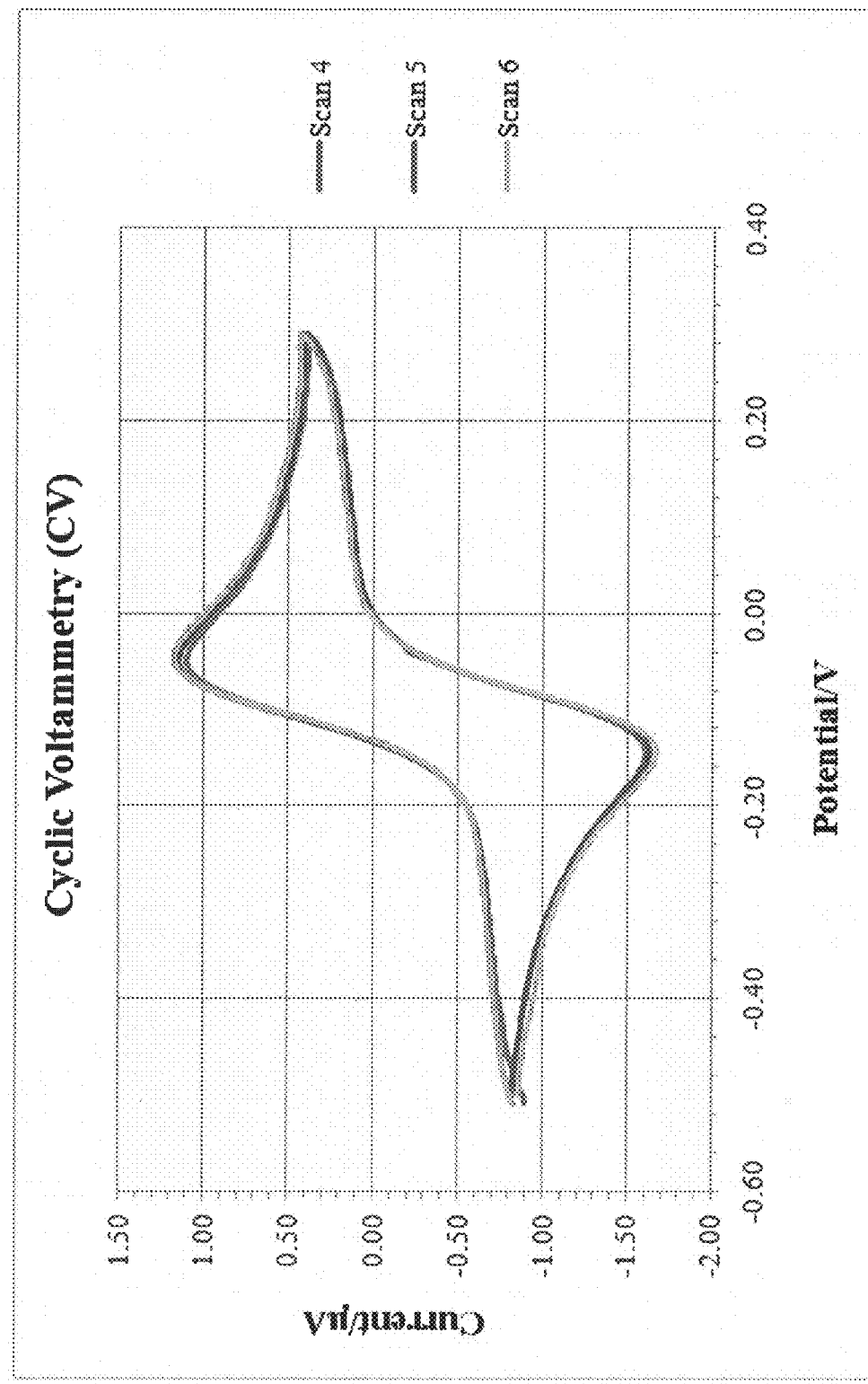
FIG. 4 is a cyclic voltammetry (CV) graph for a baseline gold (Au) electrode.

Baseline variability was chosen to be based on gold electrodes for subsequent material response evaluation. The cyclic voltammetry of six randomly picked gold electrodes from the same sputtered wafer were equivalent enough for establishment of baseline electrode variability. The electrodes showed consistent characteristics at different locations on the wafer, and multiple scans indicated stabilization of the response over the multiple scans. As shown in FIG. 4, the cyclic voltammetry using the gold electrode was a symmetrical cycle which suggested that the electrode was able to be used for the electrochemical test. After the first three scans, scans 4-6 demonstrate that the cyclic voltammetry response was stable and repeatable.

Figure 5:
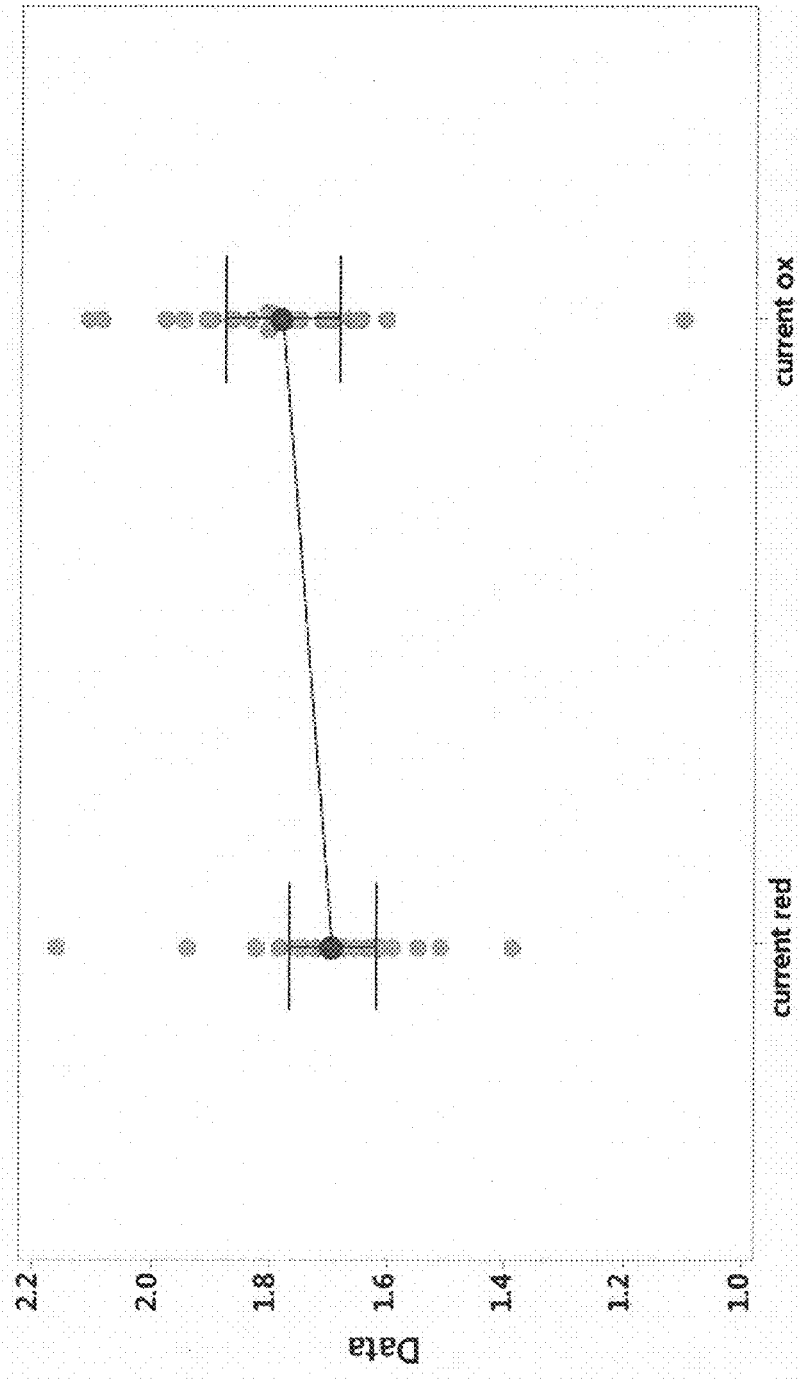
FIG. 5 is a plot of baseline reversibility of current redox versus current oxidation for a scan of the baseline gold electrode.

As an evaluation of baseline reversibility, the third scan for the gold electrode was evaluated for a significant difference in peak currents as shown in FIG. 5, as a reversible system will result in Ipa/Ipc=1. In this case, a significant difference in means was not detected, through Ipa/Ipc=1.05.

A T-Test was performed between the current redox and the current oxidation for the baseline gold electrodes to test the difference between the two samples. The results of the T-Test are shown below in Table 3:

TABLE 3

Two-Sample T-Test and CI: current red and current ox (gold)

Two-sample T for current red vs current ox

| | N | Mean | StDev | SE Mean |
|---|---|---|---|---|
| Current red | 21 | 1.693 | 0.161 | 0.035 |
| Current ox | 21 | 1.779 | 0.209 | 0.040 |

Difference = μ (current red) − μ (current ox)
Estimate for difference: −0.0858
95% CI for difference: (−0.2022, 0.0306)
T-Test of Difference = 0 vs ≠): T-Value = −1.49  P-Value = 0.144  DF = 37

As shown in Table 3 above, a significant difference in means was not detected.

Figure 6:
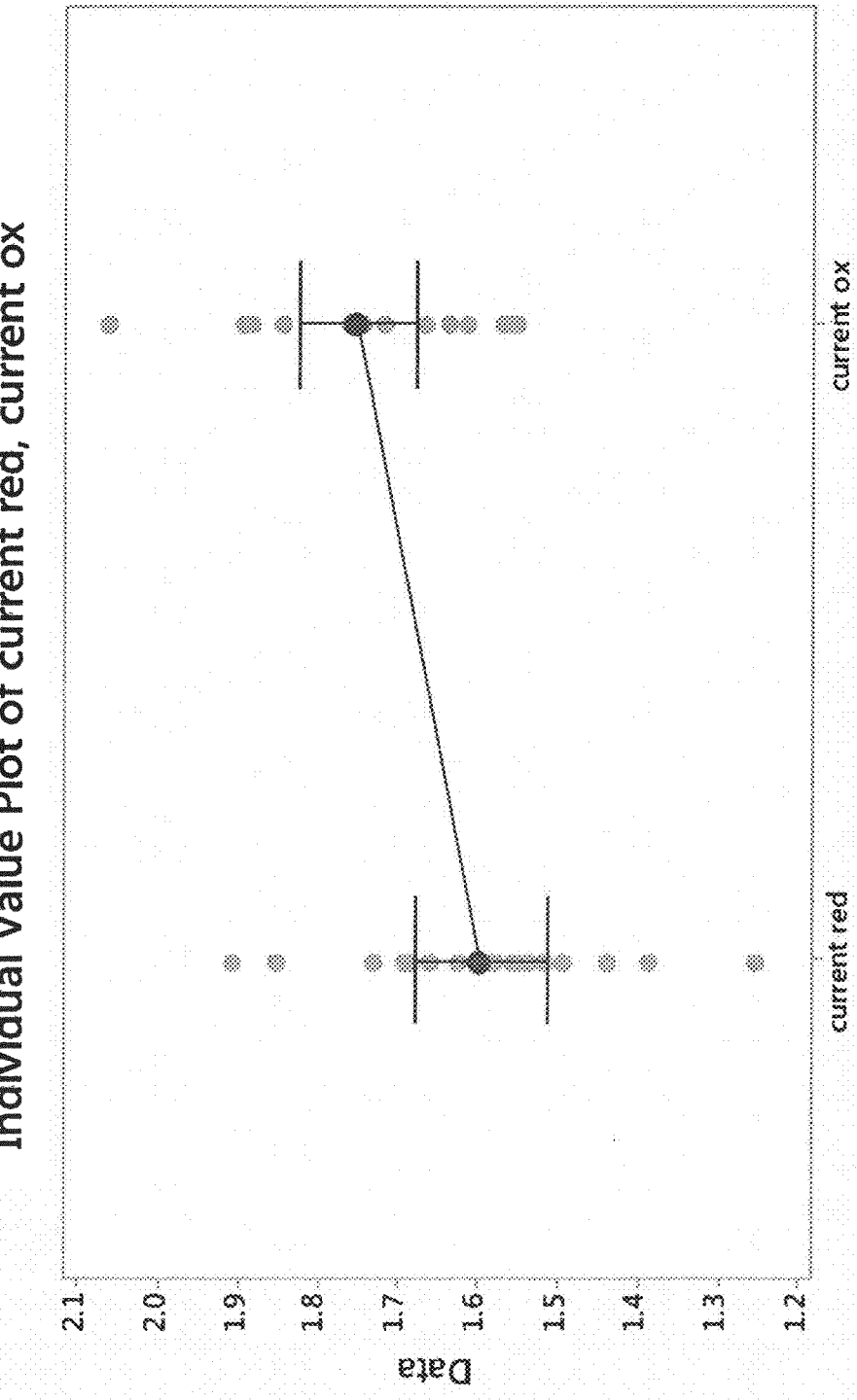
FIG. 6 is a plot of baseline reversibility of current redox versus current oxidation for a scan of a ruthenium electrode of the present disclosure.

The significance of ruthenium mean or variance differences were based on the established gold baseline variability discussed above. Based on electrode pass/fail criteria of redox response detected with 1 mM potassium ferricyanide analyte between about −500 to about 500 mV, ruthenium-based alloys demonstrated good stability and electrochemical response compared with the baseline gold electrodes. The ruthenium redox response was stable and repeatable in the range tested. As demonstrated by FIG. 6 and the results of the T-Test in Table 4 below, there appeared to be a larger amount of non-faradaic (i.e., background) current compared to gold electrode systems, since Ipa/Ipc=1.1 rather than the ideal case of Ipa/Ipc=1, possibly indicating less of a reversible system than gold.

TABLE 4

Two-Sample T-Test and CI: current red and current ox (ruthenium)

Two-sample T for current red vs current ox

| | N | Mean | StDev | SE Mean |
|---|---|---|---|---|
| Current red | 17 | 1.597 | 0.163 | 0.039 |
| Current ox | 17 | 1.753 | 0.144 | 0.035 |

Difference = μ (current red) − μ (current ox)
Estimate for difference: −0.1562
95% CI for difference: (−0.2637, 0.0486)
T-Test of Difference = 0 vs ≠): T-Value = −2.96  P-Value = 0.006  DF = 31

Figure 7A:
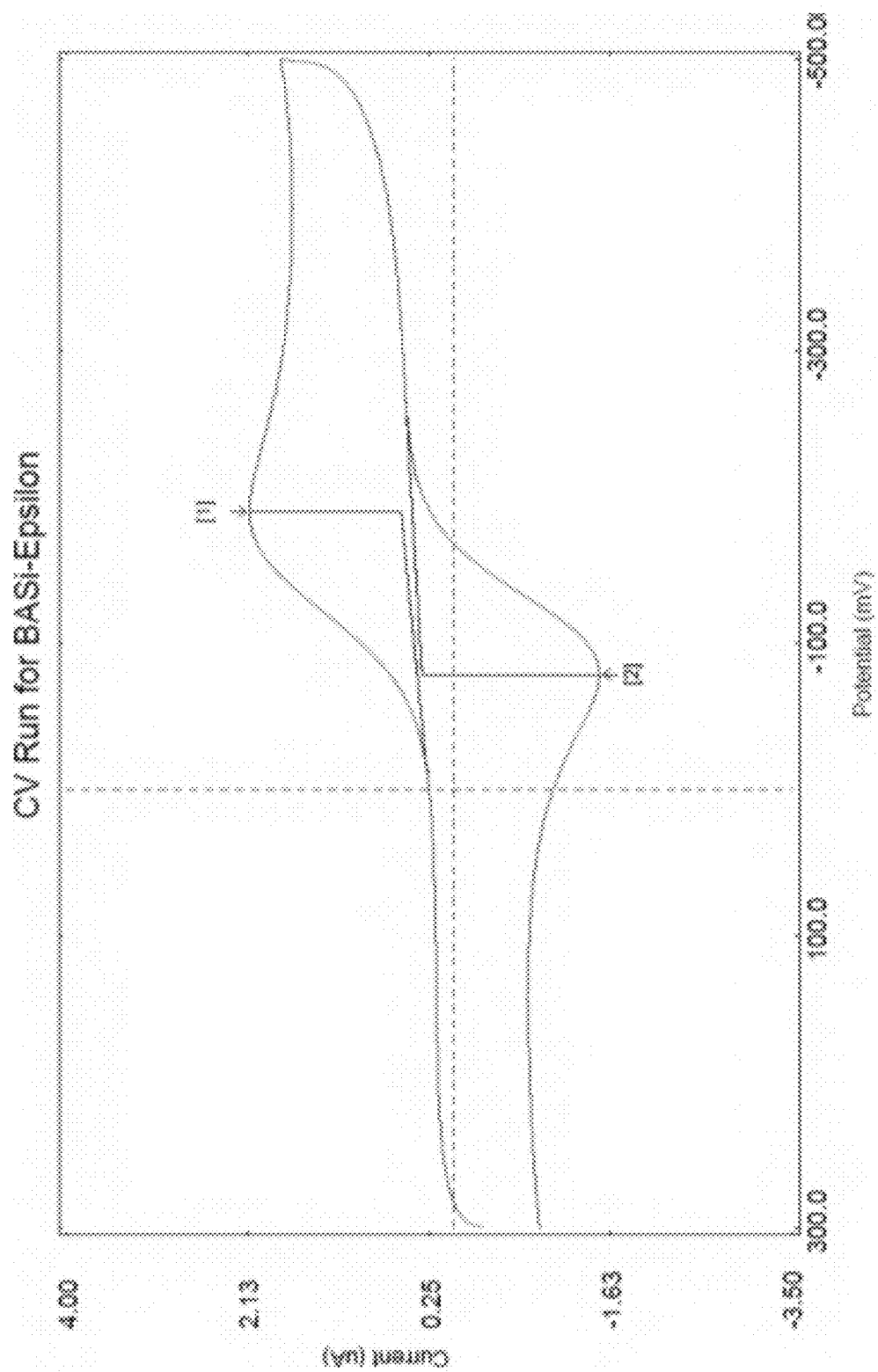
FIG. 7A is a CV graph for one scan of the ruthenium electrode of the present disclosure.
Figure 7B:
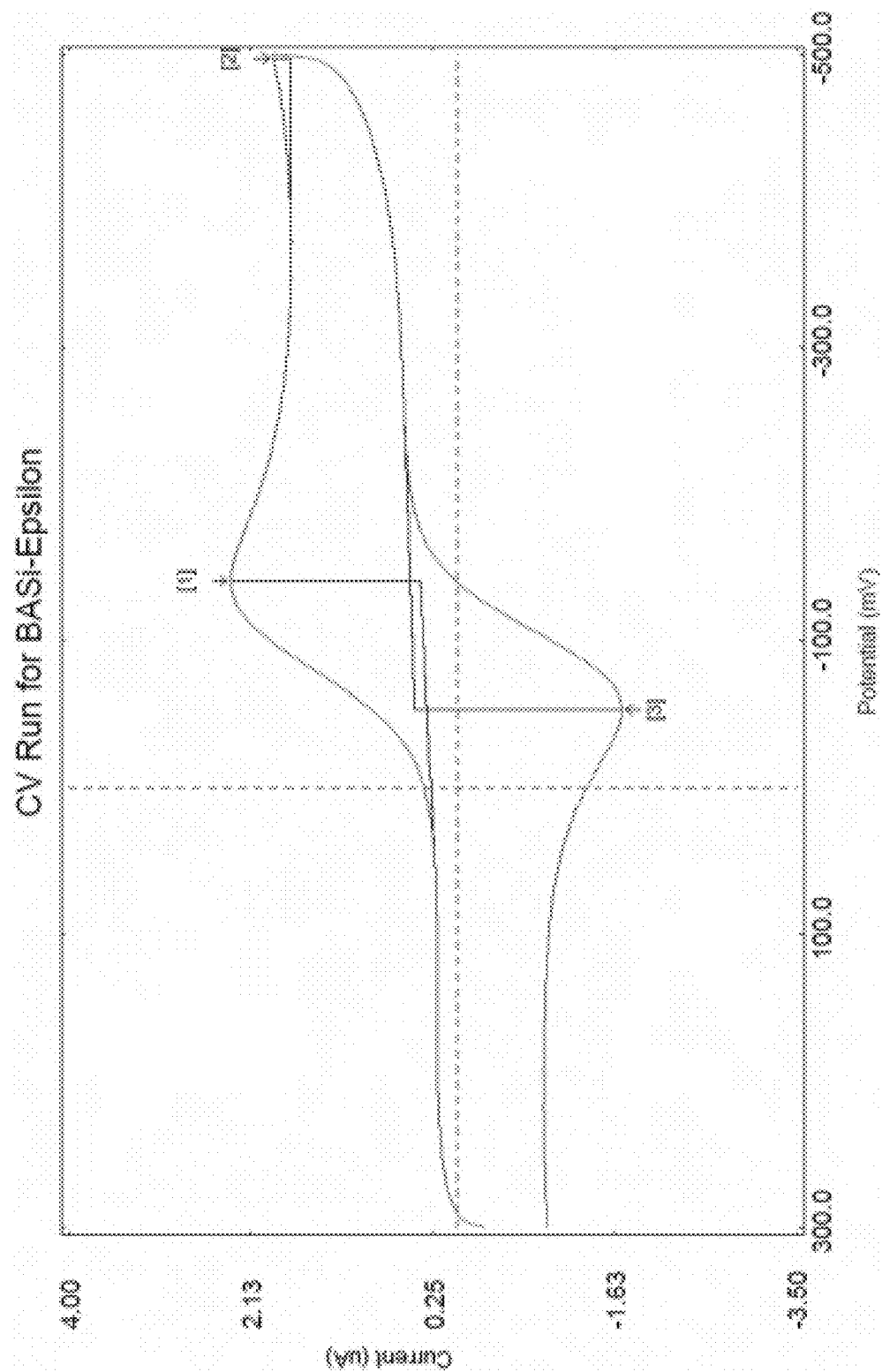
FIG. 7B is a CV graph for a second scan of the ruthenium electrode of the present disclosure.
Figure 8A:
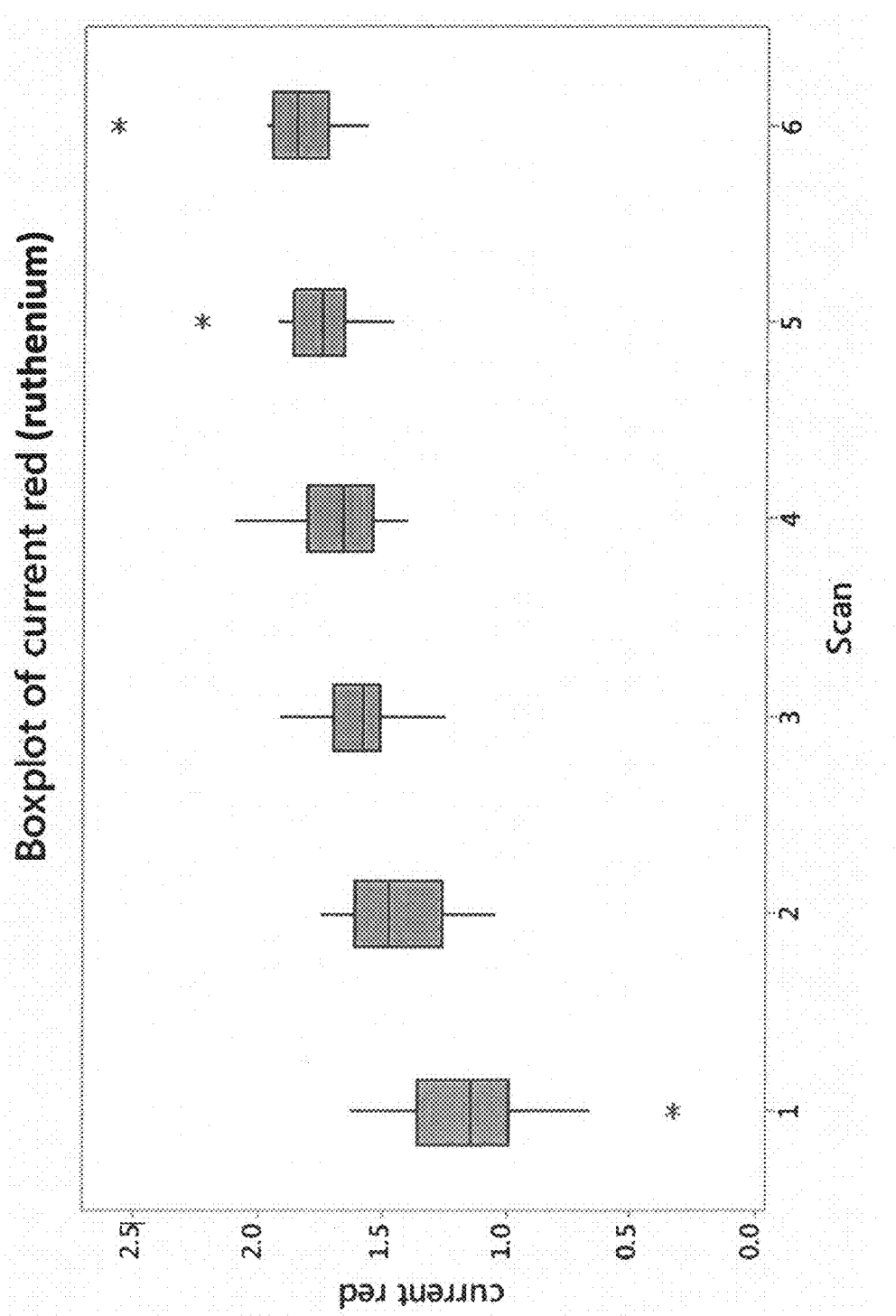
FIG. 8A is a boxplot of current redox over six scans of the ruthenium electrode of the present disclosure.
Figure 8B:
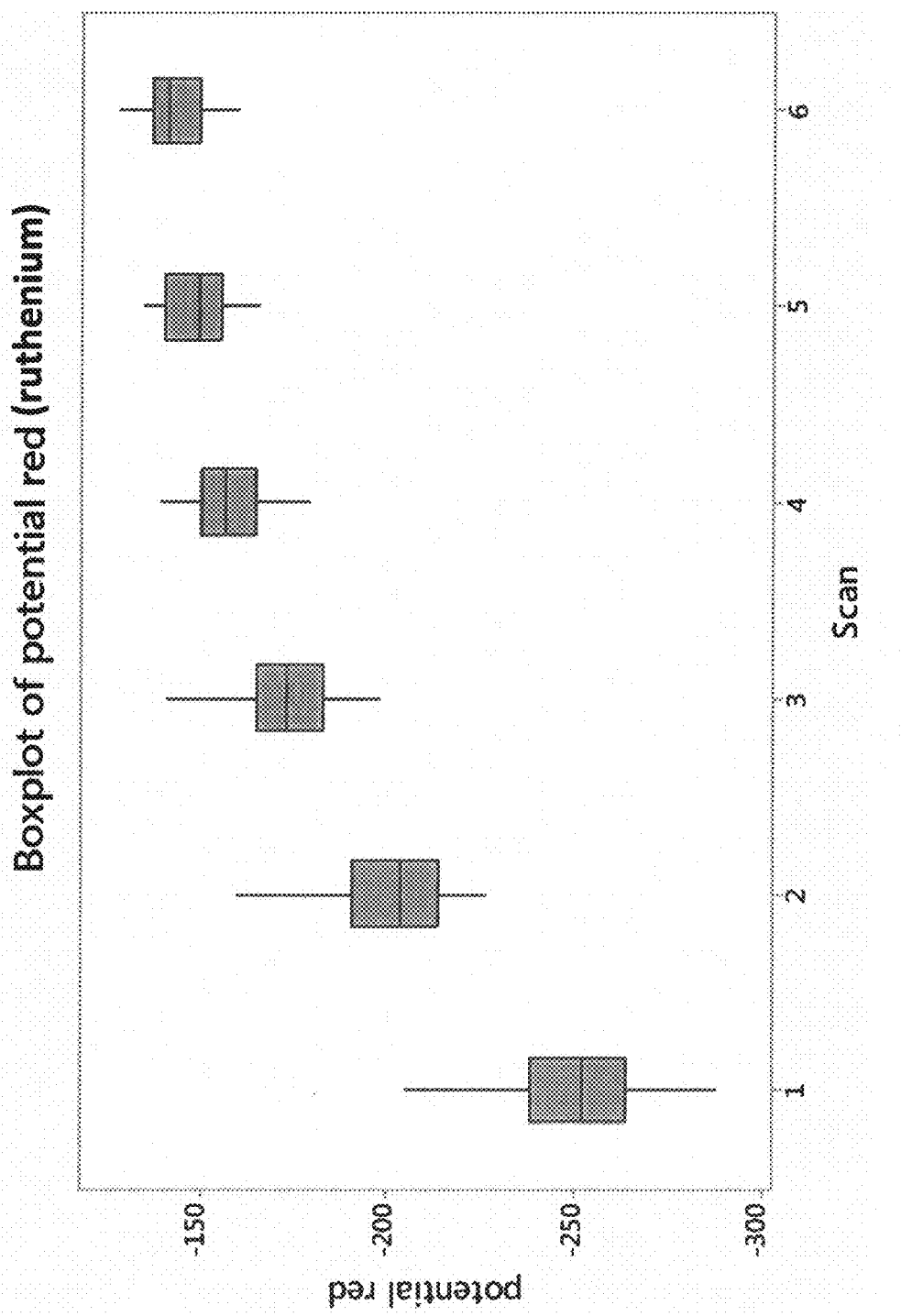
FIG. 8B is a boxplot of potential redox over six scans of the ruthenium electrode of the present disclosure.
Figure 8C:
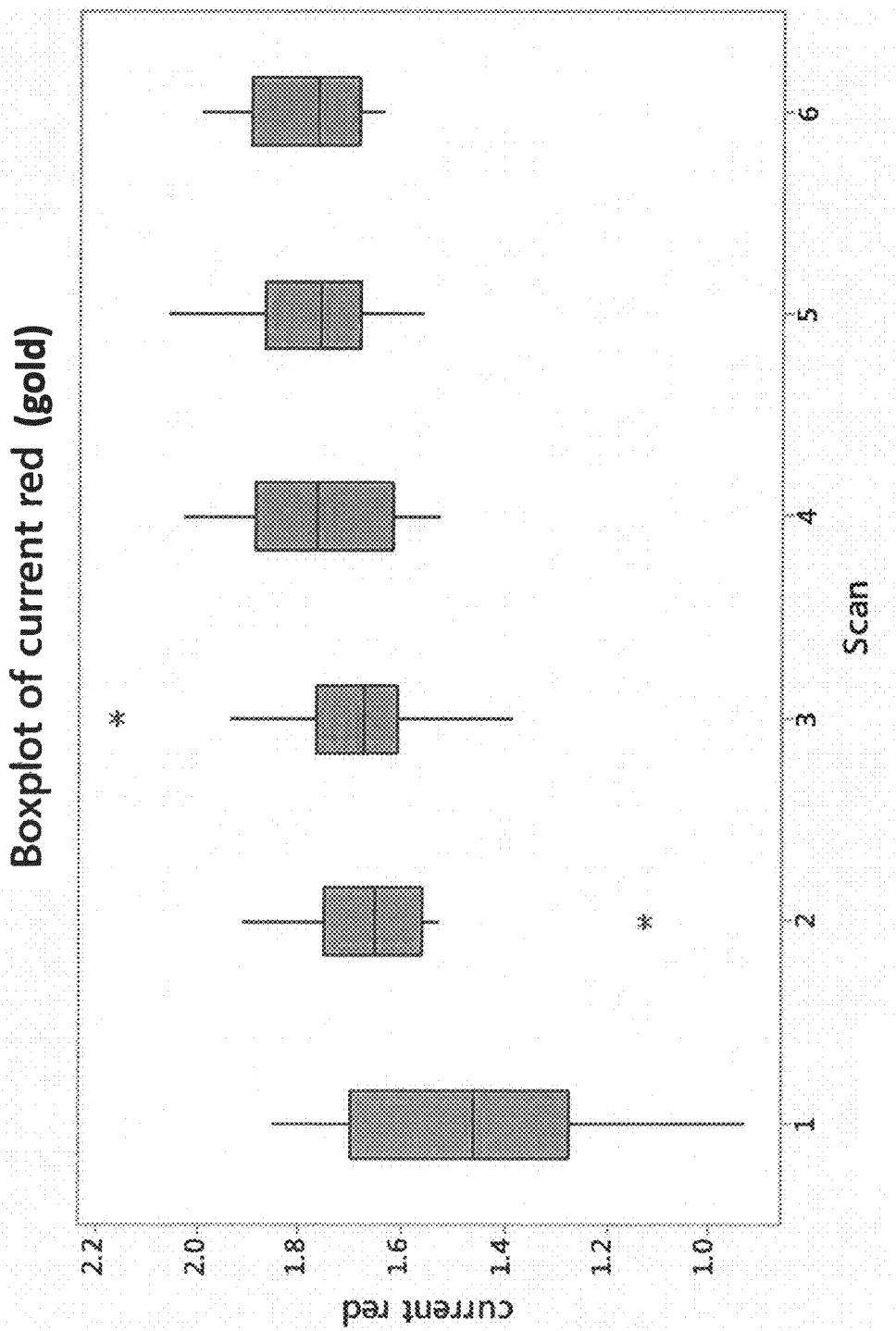
FIG. 8C is a boxplot of current redox over six scans of a gold electrode for comparison with the boxplot illustrated in FIG. 8A.
Figure 8D:
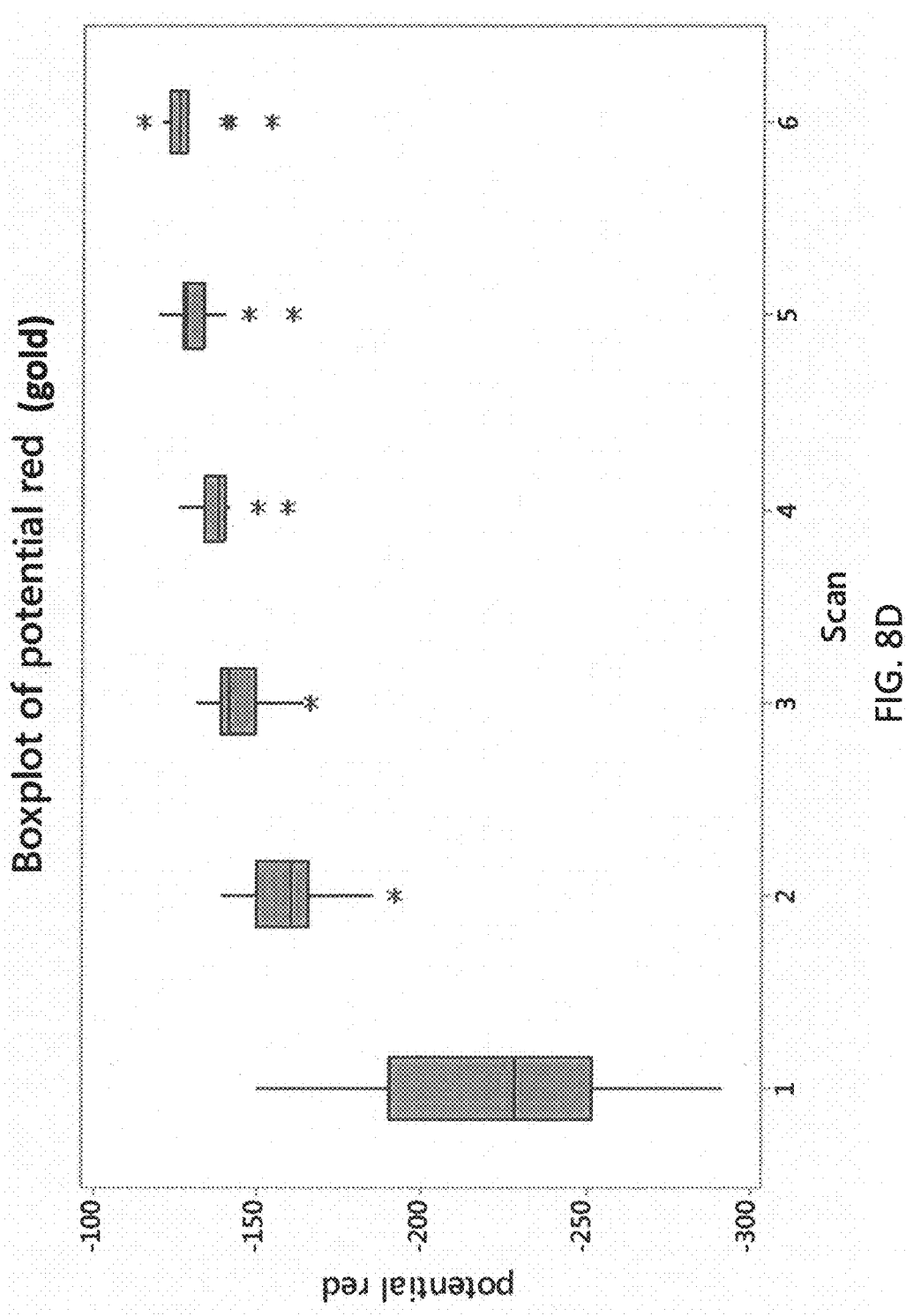
FIG. 8D is a boxplot of potential redox over six scans of a gold electrode for comparison with the boxplot illustrated in FIG. 8B.

However, the cyclic voltammetry using the ruthenium electrode in scan 2 (FIG. 7A) and scan 6 (FIG. 7B) were mostly symmetrical cycles, which suggests that the electrode was able to be used for the electrochemical test.

Moreover, as shown in FIGS. 8A-8D, ruthenium results in an increasing concave down stabilization pattern which compares favorably with the gold electrode baseline.

Example 2

The performance of existing biosensors utilizing precious metals such as gold (Au) was again compared with the performance of the ruthenium-based alloys disclosed herein, using identical test method parameters as those set forth in Example 1 above.

Figure 9:
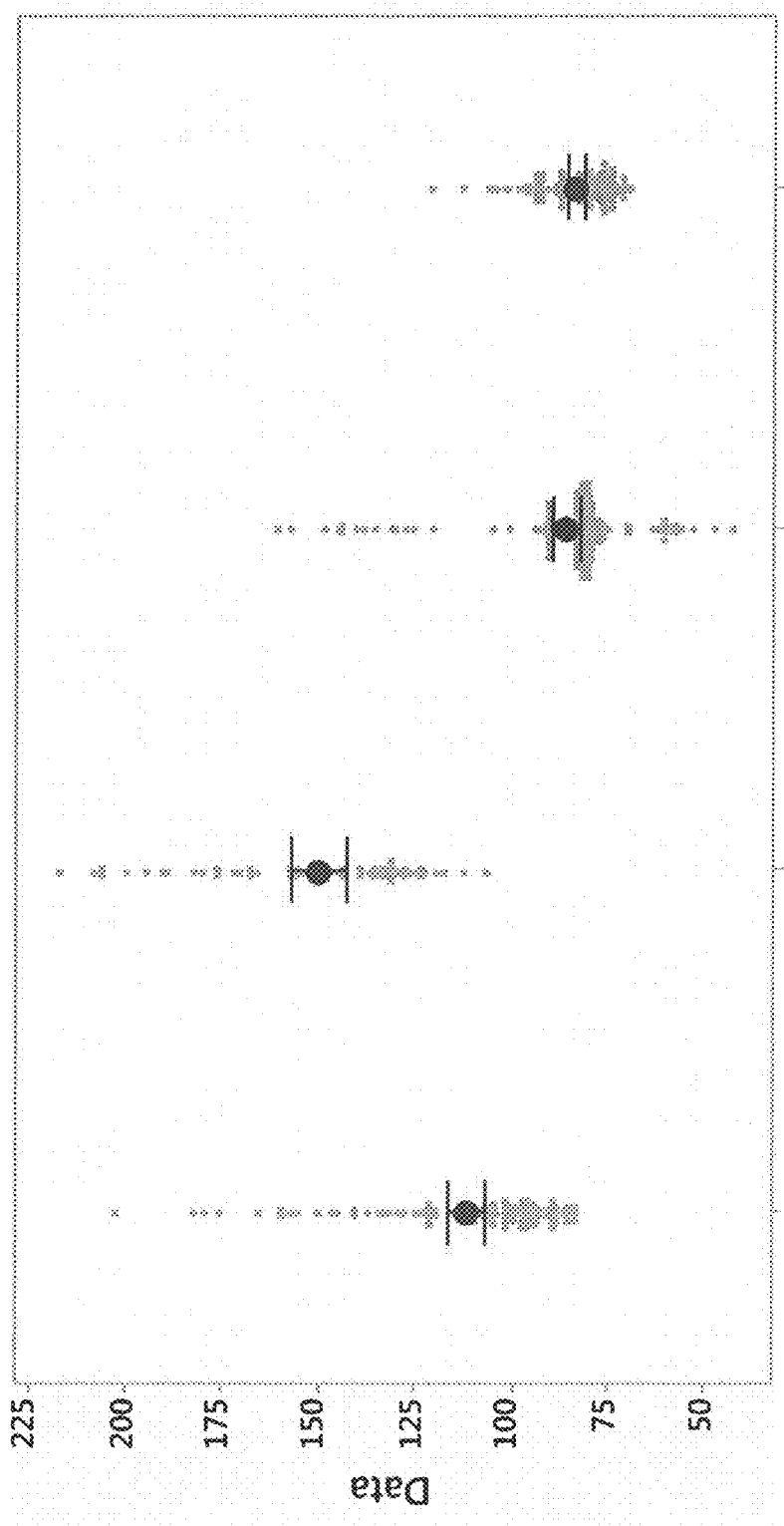
FIG. 9 is an individual value plot or ruthenium, palladium, gold, and nickel peak separations for comparison to the Nernstian ideal of 59 mV.

In Example 2, gold (Au), palladium (Pd), ruthenium (Ru) and nickel (Ni) were initially compared against the Nernstian ideal of 59 mV, which is desirable and indicative of electron transfer kinetics that are beneficial for amperometric sensing applications. As shown in FIG. 9, gold, palladium, ruthenium, and nickel all exhibit redox reactions in the system evaluated. Generally, peak potential separations were close to the Nernstian ideal of 59 mV. Ruthenium and ruthenium-based alloys show good properties in regards to the ferro/ferricyanide mediator system, with improved maneuverability and electrochemical stability in the potential range evaluated over nickel.

Binary ruthenium alloys evaluated for performance and cost are shown in Table 5 below:

TABLE 5

Binary ruthenium alloys average current response
(units in μA, 1 mM $K_4Fe(CN)_6$ analyte)

| Alloy | At % Ru Evaluated | 50-60 | 60-70 | 70-80 | 80-90 | 90-100 | Performance notes |
|---|---|---|---|---|---|---|---|
| RuAl | 0-40, 60-100 | — | 1.2073 | 1.3144 | 1.2427 | | Best results at ~65% Ru |
| RuNi | 60-100 | | 1.2759 | — | 1.3252 | | High background current |
| RuW | 0-40, 60-100 | | 1.1613 | — | 1.1928 | 1.3532 | Stable, repeatable |
| RuCr | 0-40, 60-100 | 1.1387 | — | — | 1.1481 | 1.208 | Stable, repeatable |
| RuRe | 60-100 | | 1.3635 | 1.0787 | | 1.0686 | Higher background current |

Binary nickel alloys evaluated for performance and cost are shown in Table 6 below:

TABLE 6

Binary nickel alloys average current response
(units in μA, 1 mM $K_4Fe(CN)_6$ analyte)

| Alloy | At % Ni Evaluated | 50-60 | 60-70 | 70-80 | 80-90 | 90-100 | Performance notes |
|---|---|---|---|---|---|---|---|
| NiAl | 60-100 | — | 0 | — | 0.88 | | Elimination of response in lower Ni compositions |
| NiCu | 60-100 | — | — | — | — | | Noisy, variable |
| NiTi | 60-100 | 0 | 1.683 | — | 0.6596 | 0.7878 | Comparable to NiCr at Ni > 80% composition |
| NiCr | 60-100 | — | — | — | 0.764 | | Repeatable; appears quasi-reversible |
| NiTa | 60-100 | — | — | — | — | | Weak, variable response |

By way of comparison, Table 7 below shows pure gold (Au) and palladium (Pd) metals evaluated for performance and cost:

TABLE 7

Pure metals average current response
(units in μA, 1 mM $K_4Fe(CN)_6$ analyte)

| Metal | 90-100 at % | Performance Notes |
|---|---|---|
| Au | 1.122 | Stable, low background, reversible |

TABLE 7-continued

Pure metals average current response
(units in μA, 1 mM $K_4Fe(CN)_6$ analyte)

| Metal | 90-100 at % | Performance Notes |
|---|---|---|
| Pd | 0.7217 | Strong initial response, degrades after multiple scans |

The average responses for the most promising binary ruthenium and nickel alloys tested, along with gold and palladium for comparison, is shown in Table 8 below:

TABLE 8

Average Ipa, Epa, Ipc, and Epc responses for most promising compositions

| Test | Composition | Avg. Ipa (μA) | Avg. Epa (mV) | Avg. Ipc (uA) | Avg. Epc (mV) |
|---|---|---|---|---|---|
| Au | — | 1.1228 | −55 | −1.0599 | −143 |
| RuW | 60/40 | 1.1733 | −37 | −1.242 | −120 |
| RuW | 80/20 | 1.125 | −43 | −1.1 | −133 |
| RuCr | 60/40 | 1.1387 | −47 | −1.0002 | −153 |
| RuCr | 80/20 | 1.0792 | −60 | −0.9873 | −157 |
| NiCr | 80/20 | 0.764 | −27 | −0.3566 | −120 |
| NiTi | 60/40 | 0.1683 | 97 | 0 | 0 |
| NiTi | 80/20 | 0.5493 | 33 | −0.273 | −50 |
| NiAl | 60/40 | 0 | 0 | 0 | 0 |
| NiAl | 80/20 | 0.88 | −90 | 0 | −123 |
| Pd | — | 0.7237 | −13 | −0.2777 | −118 |

Figure 10:
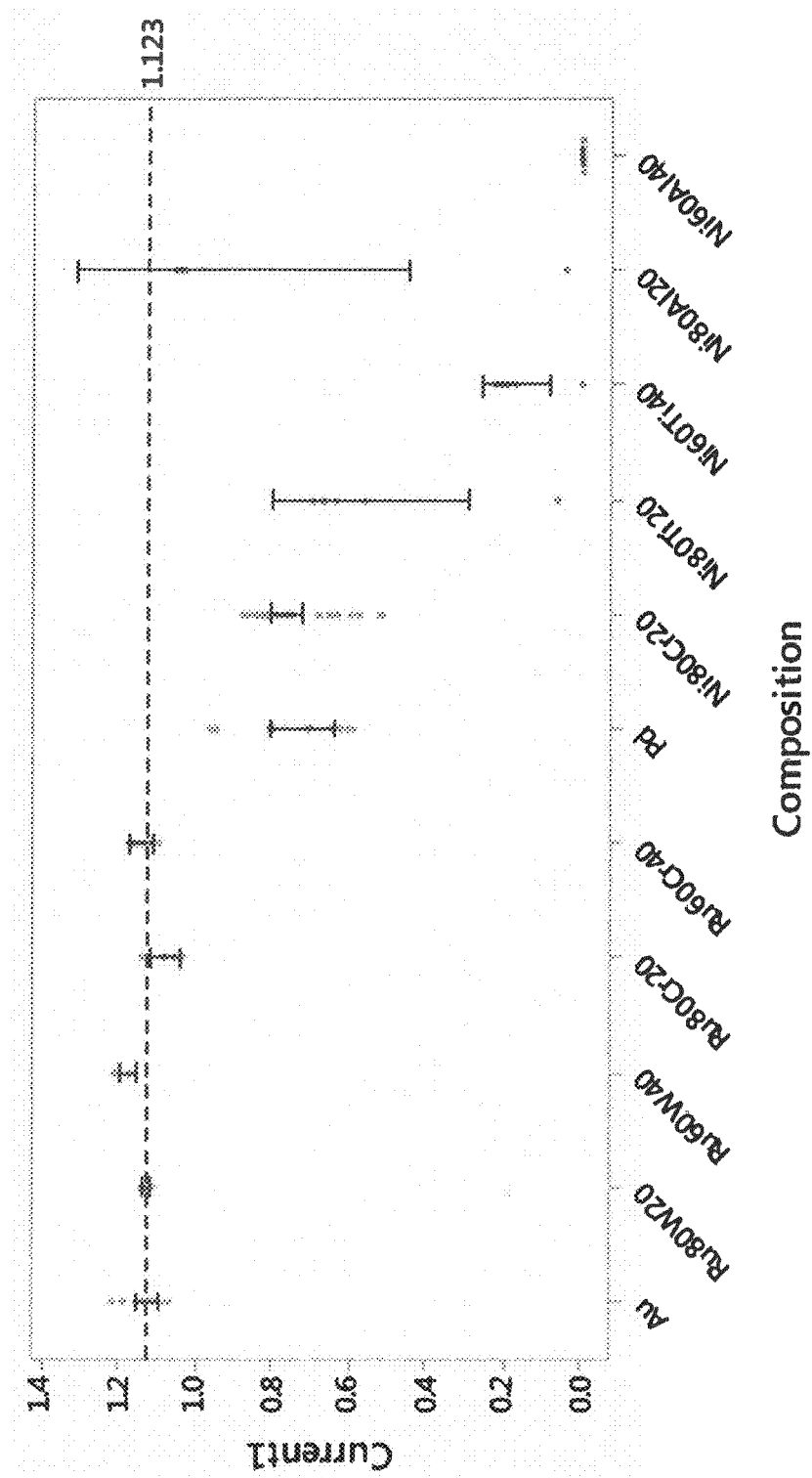
FIG. 10 is an individual value plot of current for various alloys of the present disclosure for comparison to known metals.

Ruthenium-based alloys RuW and RuCr have shown good response relative to gold with compositions of greater than 50 at % ruthenium, as presented above and as shown in FIG. 10.

Thus, in view of the aforementioned Examples 1 and 2 discussed above, screening results indicate that non-precious metal alloys, including nickel and/or ruthenium (note that though ruthenium may be classified as a precious metal, in this context it qualifies as a candidate based on cost), advantageously comparable responses and performance to expensive pure metals such as gold and palladium. In addition, these non-precious metal alloys may further be optimized for corrosion resistance through the addition of titanium (Ti), tantalum (Ta), and chromium (Cr). Moreover, these non-precious metal alloys may further be optimized for cost through the addition of nickel (Ni), titanium (Ti), molybdenum (Mo), aluminum (Al), tin (Sn), etc.

Particular alloys that have responses comparable to gold and exceeding palladium or NiCr performance include RuW (Ru>50%) and RuCr (Ru>50%).

In addition, ternary alloys have been tested with the same combination of the above elements (e.g., RuCrW and RuAlNi). These ternary alloys have advantages when designing for certain material properties (e.g., ductility, corrosion resistance, heat resistance).

The ruthenium metal and the ruthenium-based alloys of the present disclosure have been described as being useful in biosensor/electrode type applications. However, it should be understood the alloys disclosed herein may be useful in any sensor article or device that, as a result of a chemical interaction or process between an analyte and the sensor, transforms chemical or biochemical information of a quantitative or qualitative type into a analytically useful signal. For example, it is contemplated that the ruthenium-based alloys disclosed herein may be included in articles useful in automotive, indoor air quality (IAQ), food, agriculture, medical, water treatment, environmental, industrial safety, utilities (e.g., gas, electric), petrochemical, steel, military, and aerospace applications and markets.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:

1. A method of using a biosensor for measuring an analyte in a biological fluid, comprising:
exposing a first electrode of the biosensor to the biological fluid,
wherein the biosensor is configured to output an electronic signal that corresponds to a concentration of the analyte in the biological fluid,
wherein the first electrode comprises a ruthenium based metal alloy on a surface of a substrate,
wherein the ruthenium based metal alloy consists essentially of ruthenium and at least one alloying element selected from the group consisting of aluminum, chromium, copper, nickel, rhenium, and tungsten.

2. The method of claim 1, wherein the ruthenium based metal alloy comprises from about 5 at % to less than 100 at % ruthenium.

3. The method of claim 1, wherein the biological fluid is exposed to the first electrode by applying the biological fluid to a reaction chamber of the biosensor, wherein the reaction chamber is in contact with the first electrode.

4. The method of claim 1, wherein the electronic signal is based on a reduction/oxidation reaction between the analyte and a reagent layer arranged on the first electrode.

5. The method of claim 1, wherein the ruthenium based metal alloy is a binary alloy consisting essentially of ruthenium and a first alloying element, wherein the ruthenium based metal alloy comprises from about from about 5 at % to less than 100 at % ruthenium, and wherein the first alloying element consists of aluminum, chromium, copper, nickel, rhenium, or tungsten.

6. The method of claim 1, wherein the ruthenium based metal alloy is a ternary alloy consisting essentially of ruthenium, a first alloying element, and a second alloying element, wherein the ruthenium based metal alloy comprises from about from about 5 at % to less than 100 at % ruthenium, and wherein the first alloying element and the second alloying element are each selected from the group consisting of aluminum, chromium, copper, nickel, rhenium, and tungsten.

7. The method of claim 1, wherein the ruthenium based metal alloy forms an electrode having a thickness between 10 nanometers and 100 nanometers, and wherein the electrode has an electrical conductivity less than 100 ohms/square ($\Omega$/sq) at the thickness.

8. A method for measuring an analyte in a fluid sample comprising:
providing a sensor configured to receive and measure a concentration of the analyte based on a reduction/oxidation reaction of the analyte at a working electrode of the sensor;
applying the fluid sample to a reaction chamber of the sensor, wherein the fluid sample contacts the working electrode through the reaction chamber; and
receiving a signal output from the sensor indicating the concentration of the analyte,
wherein the working electrode comprises a ruthenium based metal alloy, wherein the ruthenium metal based alloy is a binary alloy and consists essentially of ruthenium and a first alloying element,
wherein the ruthenium based metal alloy comprises from about 5 at % to about 95 at % ruthenium, and
wherein the first alloying element consists of aluminum, chromium, copper, nickel, rhenium, or tungsten.

9. The method of claim 8, wherein a reagent layer is arranged on the working electrode and comprises an enzyme for the reduction/oxidation reaction.

10. The method of claim 8, wherein the fluid sample is blood and the analyte is glucose.

11. The method of claim 8, wherein the working electrode has an electrical conductivity that is less than about 100 ohms/square.

12. The method of claim 8, wherein the first alloying element consists of either chromium or tungsten, and wherein the ruthenium based metal alloy consists essentially of about 15 at % to about 25 at % of either chromium or tungsten.

13. The method of claim 8, wherein the first alloying element consists of nickel, and wherein the ruthenium based metal alloy consists essentially of about 75 at % to about 95 at % of nickel.

14. The method of claim 8, wherein the first alloying element consists of aluminum, and wherein the ruthenium based metal alloy consists essentially of about 30 at % to about 40 at % of aluminum.

15. The method of claim 8, wherein the first alloying element consists of either chromium or tungsten, and wherein the ruthenium based metal alloy consists essentially of about 35 at % to about 45 at % of either chromium or tungsten.

16. A method for measuring an analyte in a fluid sample comprising:
providing a sensor configured to receive and measure a concentration of the analyte based on a reduction/oxidation reaction of the analyte at a working electrode of the sensor;
applying the fluid sample to a reaction chamber of the sensor, wherein the fluid sample contacts the working electrode through the reaction chamber; and
receiving a signal output from the sensor indicating the concentration of the analyte,
wherein the working electrode comprises a ruthenium based metal alloy, wherein the ruthenium metal based alloy is a ternary alloy and consists essentially of ruthenium, a first alloying element, and a second alloying element, wherein the ruthenium based metal alloy comprises from about 5 at % to about 95 at % ruthenium, and wherein the first alloying element and the second alloying element are each selected from the group consisting of aluminum, chromium, copper, nickel, rhenium, or tungsten.

17. The method of claim 16, wherein a ratio of the weight of the first alloying element to the weight of the second alloying element in the ruthenium based metal alloy is between 1 and 2.

18. The method of claim 16, wherein a reagent layer is arranged on the working electrode and comprises an enzyme for the reduction/oxidation reaction.

19. The method of claim 16, wherein the working electrode has an electrical conductivity that is less than about 100 ohms/square.

20. The method of claim 16, wherein the fluid sample is blood and the analyte is glucose.

\* \* \* \* \*